(12) United States Patent
Waugh

(10) Patent No.: US 8,815,954 B2
(45) Date of Patent: Aug. 26, 2014

(54) ARGININE HETEROMERS FOR TOPICAL ADMINISTRATION

(75) Inventor: Jacob M. Waugh, Mountain View, CA (US)

(73) Assignee: Revance Therapeutics, Inc., Newark, CA (US)

( * ) Notice: Subject to any disclaimer, the term of this patent is extended or adjusted under 35 U.S.C. 154(b) by 2 days.

(21) Appl. No.: 11/617,551

(22) Filed: Dec. 28, 2006

(65) Prior Publication Data

US 2007/0265233 A1    Nov. 15, 2007

Related U.S. Application Data

(60) Provisional application No. 60/755,203, filed on Dec. 30, 2005.

(51) Int. Cl.
 *A61K 31/07*    (2006.01)
 *A23L 1/30*    (2006.01)

(52) U.S. Cl.
 USPC ................................ 514/725; 426/72; 426/73

(58) Field of Classification Search
 USPC ................ 514/167, 458, 474, 558, 725, 182;
 562/553; 426/72, 73; 552/544
 See application file for complete search history.

(56) References Cited

U.S. PATENT DOCUMENTS

| | | | |
|---|---|---|---|
| 4,101,549 A | 7/1978 | Focella | |
| 4,877,805 A | 10/1989 | Kligman | |
| 4,888,342 A | 12/1989 | Kligman | |
| 5,334,713 A * | 8/1994 | Hattori et al. | 540/113 |
| 5,362,418 A * | 11/1994 | Yamasaki et al. | 516/40 |
| 5,391,753 A | 2/1995 | Chandraratna | |
| 5,399,561 A | 3/1995 | Chandraratna | |
| 5,399,586 A | 3/1995 | Davies et al. | |
| 5,407,937 A | 4/1995 | Chandraratna | |
| 5,414,007 A | 5/1995 | Chandraratna | |
| 5,426,118 A | 6/1995 | Chandraratna et al. | |
| 5,434,173 A | 7/1995 | Chandraratna | |
| 5,451,605 A | 9/1995 | Chandraratna et al. | |
| 5,455,265 A | 10/1995 | Chandraratna | |
| 5,468,879 A | 11/1995 | Chandraratna | |
| 5,470,999 A | 11/1995 | Chandraratna | |

(Continued)

FOREIGN PATENT DOCUMENTS

| DE | 202004016689 | 2/2005 |
|---|---|---|
| EP | 0379367 | 7/1990 |

(Continued)

OTHER PUBLICATIONS

JB Chazan et al., "Free Radicals and Vitamin E.," Cah Nutri. Diet., 1987 22(1):66-76.

(Continued)

*Primary Examiner* — T. Victor Oh
(74) *Attorney, Agent, or Firm* — Kenneth H. Sonnenfeld; Joseph D. Eng, Jr.; King & Spalding LLP

(57) ABSTRACT

The invention is directed to a strategy for providing therapeutic or cosmetic benefit to skin by topically applying arginine chemically bound to a second (non-oligoarginine) compound in order to increase transepithelial delivery of arginine through a combination of increased solubility and flux across the skin. The arginine heteromers of the invention can add other complementary or beneficial properties for the skin beyond those that are arginine-related.

12 Claims, 4 Drawing Sheets

(56) References Cited

U.S. PATENT DOCUMENTS

| | | | |
|---|---|---|---|
| 5,498,755 A | 3/1996 | Chandraratna et al. | |
| 5,514,825 A | 5/1996 | Vuligonda et al. | |
| 5,516,904 A | 5/1996 | Chandraratna | |
| 5,534,516 A | 7/1996 | Chandraratna | |
| 5,556,996 A | 9/1996 | Beard et al. | |
| 5,559,248 A | 9/1996 | Starrett, Jr. et al. | |
| 5,599,819 A | 2/1997 | Chandraratna | |
| 5,602,130 A | 2/1997 | Chandraratna | |
| 5,602,135 A | 2/1997 | Chandraratna | |
| 5,605,915 A | 2/1997 | Vuligonda et al. | |
| 5,616,597 A | 4/1997 | Chandraratna | |
| 5,616,712 A | 4/1997 | Teng et al. | |
| 5,618,836 A | 4/1997 | Chandraratna et al. | |
| 5,618,839 A | 4/1997 | Starrett, Jr. et al. | |
| 5,618,931 A | 4/1997 | Beard et al. | |
| 5,618,943 A | 4/1997 | Vuligonda et al. | |
| 5,648,385 A | 7/1997 | Starrett, Jr. et al. | |
| 5,648,503 A | 7/1997 | Vuligonda et al. | |
| 5,648,514 A | 7/1997 | Johnson et al. | |
| 5,648,563 A | 7/1997 | Buck et al. | |
| 5,663,347 A | 9/1997 | Chandraratna | |
| 5,663,357 A | 9/1997 | Teng et al. | |
| 5,663,367 A | 9/1997 | Vuligonda et al. | |
| 5,668,175 A | 9/1997 | Evans et al. | |
| 5,672,710 A | 9/1997 | Beard et al. | |
| 5,675,024 A | 10/1997 | Teng et al. | |
| 5,675,033 A | 10/1997 | Vuligonda et al. | |
| 5,677,320 A | 10/1997 | Chandraratna | |
| 5,677,323 A | 10/1997 | Chandraratna | |
| 5,677,451 A | 10/1997 | Chandraratna | |
| 5,688,957 A | 11/1997 | Teng et al. | |
| 5,696,162 A | 12/1997 | Chandraratna | |
| 5,698,700 A | 12/1997 | Song et al. | |
| 6,794,375 B2 * | 9/2004 | Sarama et al. | 514/182 |
| 6,864,386 B1 | 3/2005 | Zhang | |

FOREIGN PATENT DOCUMENTS

| | | | |
|---|---|---|---|
| EP | 0 659 755 | | 6/1995 |
| EP | 0 756 862 | | 2/1997 |
| EP | 1 264 590 | | 12/2002 |
| FR | 2 740 453 | | 4/1997 |
| GB | 2 216 522 | | 10/1989 |
| JP | 58-203982 | * | 5/1982 |
| JP | 58-203982 | | 11/1983 |
| JP | 09241156 | * | 9/1997 |
| JP | 2000-128725 | | 5/2000 |
| JP | 2003-520846 | | 7/2003 |
| JP | 2008-515770 | | 1/2006 |
| WO | WO 99/13717 | | 3/1999 |
| WO | WO 01/13957 | | 3/2001 |
| WO | WO 03/072039 | | 9/2003 |

OTHER PUBLICATIONS

International Cosmetic Ingredient Dictionary and Handbook, 7th ed., 1997, vol. 2, p. 1567.

Lu et al., "Reactivity of Common Functional Groups with Urethanes: Models for Reactive Compatibilization of Thermoplastic Polyurethane Blends," Journal of Polymer Science: Part A: Polymer Chemistry 40, pp. 2310-2328, 2002.

Meilsi et al., "Galactosyl Derivatives of L-Arginine: Synthesis, Stability, Cell Permeation, and Notric Oxide Production in Pituitary GH3 Cells," Journal of Medicinal Chemistry, vol. 49, pp. 4826-4833, Jan. 2006.

Sigurdsson et al., "A Mild and Simple Method for the Preparation of Isocyanates from Aliphatic Amines Using Trichloromethyl Chloroformate. Synthesis of an Isocyanate Containing an Activated Disulfide," J. Org. Chem., 61, pp. 3883-3884, 1996.

Solomons et al., "Synthesis of Ethers: Ethers by Intermolecular Dehydration of Alcohols," Chapter 11.11A, Organic Chemistry, $9^{th}$ edition, pp. 487-491, 2008.

Solomons et al., "Reaction of Amines with Nitrous Acid: Reactions of Primary Aliphatic Amines with Nitrous Acid," Chapter 20.6A, Organic Chemistry, $9^{th}$ edition, pp. 921-923, 2008.

Solomons et al., "Alcohols by Reduction of Carbonyl Compunds," Chapter 12.3, Organic Chemistry, $9^{th}$ edition, pp. 517-520, 2008.

Wada et al., "Enzymatic Sythesis of N-acyl-L-amino in Glycerol-water System Using Acylase I from Pig Kidney," Journal of the American Oil Chemists Society, vol. 79, No. 1, pp. 41-46, 2002.

Revance Therapeutics, Inc., Supplemental European Search Report, Feb. 14, 2012, 12 pages.

Kemp. D, and F. Vellacio, Organic Chemistry, Worth Publishers, 1980, pp. 86-87, 277.

Smith, M.B., and J. March, March's Advanced Organic Chemistry:Reactions, Mechanisms, and Structure, 5th Ed. (2001), pp. 506-510.

Thomas, M. et al. "Synthesis and Photochemical Behaviour of a T-T Dimer Containing an Amide Linkage," Nucleosides, Nucleotides & Nucleic Acids, 20(4-7), 927-929 (2001).

* cited by examiner all R = H or BocArg(Boc$_2$)O ester all G = H or Arg·O ester

ARGININE HETEROMERS FOR TOPICAL ADMINISTRATION

This application claims the benefit of priority to U.S. Provisional Application No. 60/755,203 filed Dec. 30, 2005, and incorporates by reference this entire provisional application in its entirety.

FIELD OF THE INVENTION

The invention relates to arginine heteromers which have an improved ability to penetrate mammalian skin and provide beneficial effects for the health and appearance of skin.

BACKGROUND OF THE INVENTION

L-Arginine is a naturally occurring amino acid which plays many essential roles in the human body. One of these roles is as a substrate for nitric oxide synthase (NOS). Under normal conditions in the human body, nitric oxide (NO) has a half-life of only 3-5 seconds due to its swift inactivation by oxyhemoglobin when forming methemoglobin. Cyclic GMP is a downstream product of NO and controls most of the biological effects of NO, while the nitric oxide synthase (NOS) family of enzymes controls NO production. The three main types of NOS are: 1) inducible (iNOS); 2) neuronal (nNOS); and 3) endothelial (eNOS), all of which are found in the skin. All three of these isoforms require oxygen and nicotinamide adenine dinucleotide phosphate (NADPH) as substrates. Asymmetric dimethyl L-arginine (ADMA) is a basal inhibitor of the NOS family, and elevated levels of this substance have been found in cases of hypertension, hypercholesterolemia and other diseases associated with impaired vasodilatation. Elevating the concentration of L-arginine has been shown to overcome the inhibitory effect of ADMA without leading to increased NO production.

NO is known to play an important role in the physiology of the skin with effects on the microvasculature and blood flow, maintenance of barrier function, inflammatory skin conditions such as psoriasis, response to ultraviolet light and wound healing. Increased tissue NO concentration stimulates local vasodilatation and angiogenesis. However, NO diffuses freely so that it is difficult to maintain effective concentrations in the skin. An alternate strategy would be to elevate arginine concentration to increase the amount of substrate for NOS to use in the production of NO. However, arginine by itself has very poor skin penetration. One solution to this problem in other tissues has been to link L-arginine into oligomers from 7 to 15 units in length (oligoarginine). These compounds can effectively penetrate skin and increase concentrations of NO and have even been shown to transport covalently bound agents across cytoplasmic membranes (Cosmetic Formulations containing L-Arginine Oligomers, WO 03/072039 A2). However, it was not clear whether these benefits were due to the relatively unique transport properties of oligoarginine.

A specific example of the importance of angiogenesis in the skin is in the maintenance of healthy hair follicles. During the follicle life cycle, angiogenesis is largely controlled by a balance between pro- and anti-angiogenic factors. It has been shown that the anagen phase is especially dependent on pro-angiogenic factors to stimulate the increased blood flow necessary for the increased nutritional needs of the follicle (Cosmetic Formulations containing L-Arginine Oligomers, WO 03/072039 A2).

The invention described herein is directed to a strategy for providing therapeutic or cosmetic benefit to skin by topically applying arginine chemically bound to a second (non-oligoarginine) compound in order to increase transepithelial delivery of arginine through a combination of increased solubility and flux across the skin. The arginine heteromers of the invention can also provide other complementary or beneficial properties for the skin beyond those that are arginine-related.

SUMMARY OF THE INVENTION

This invention provides a strategy for providing therapeutic or cosmetic benefit to skin by topically applying an arginine heteromer. An arginine heteromer is a single arginine molecule chemically bound to a second (non-oligoarginine) compound in order to increase transepithelial delivery of the arginine heteromer through one or more of increased solubility and flux across the skin. The general structure of the arginine heteromer is given in formula I:

Formula I $$A\text{-}R \qquad \qquad I$$

Where A is a single arginine molecule having a free guanidine group and R is a second compound which is an organic molecule that is not arginine or oligo-arginine. The arginine molecule may be bound to the second compound through either its carboxy or amino group and the guanidino group of the arginine remains free. The arginine heteromer may have greater flux across the skin than monomeric arginine alone.

The second compound of the arginine heteromers of the invention can add other complementary or beneficial properties for the skin beyond those that are arginine-related. More specifically, the second compound of the heteromer can provide other benefits such as, antioxidant capacity, angiogenesis augmentation, reduction in the symptoms of acne, reduction of glandular secretions, reduction of the effects of aging, or wrinkle reduction. One example of a specific embodiment of the invention is arginine bound to vitamin E by an ester linkage. Also, relative to oligomer strategies, these arginine heteromers offer significant safety and cost benefits.

Another embodiment of the invention provides a method for providing a beneficial effect to skin comprising topically applying a composition comprising an arginine heteromer of Formula I. The beneficial effect can include, but is not limited to, reducing or preventing damage caused by sunlight, providing antioxidant activity, reducing the appearance of fine line and wrinkles in the skin, reducing glandular secretions, reducing the effects of aging, treating acne and inducing angiogenesis in hair follicles.

DETAILED DESCRIPTION OF THE INVENTION

Figure 1:
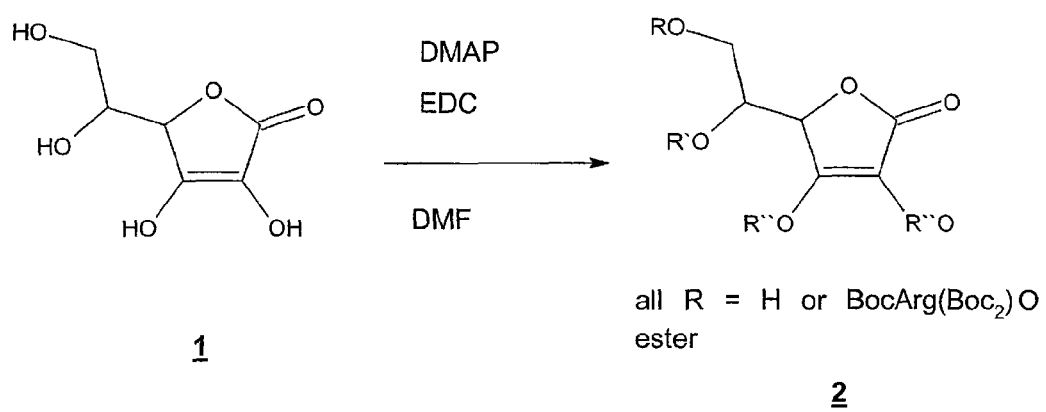
FIG. 1. Diagram showing the formation of arginine heteromer from vitamin C where R is hydrogen or Boc protected arginine.
Figure 2:
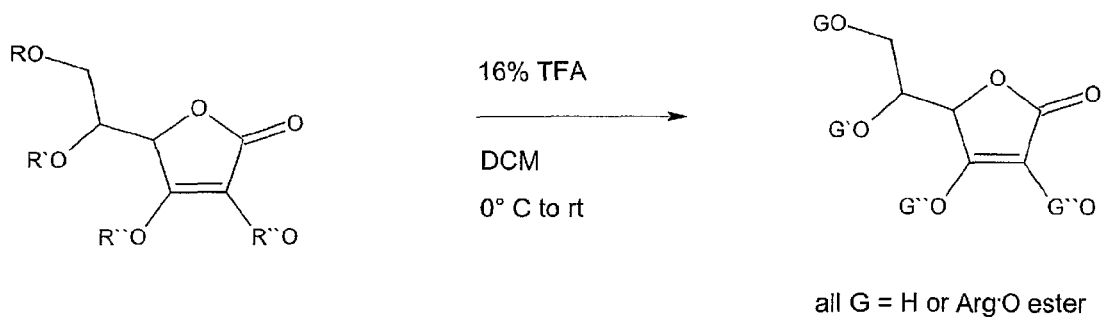
FIG. 2. Diagram showing the formation of arginine heteromer from vitamin C where G is hydrogen or deprotected arginine.
Figure 3:
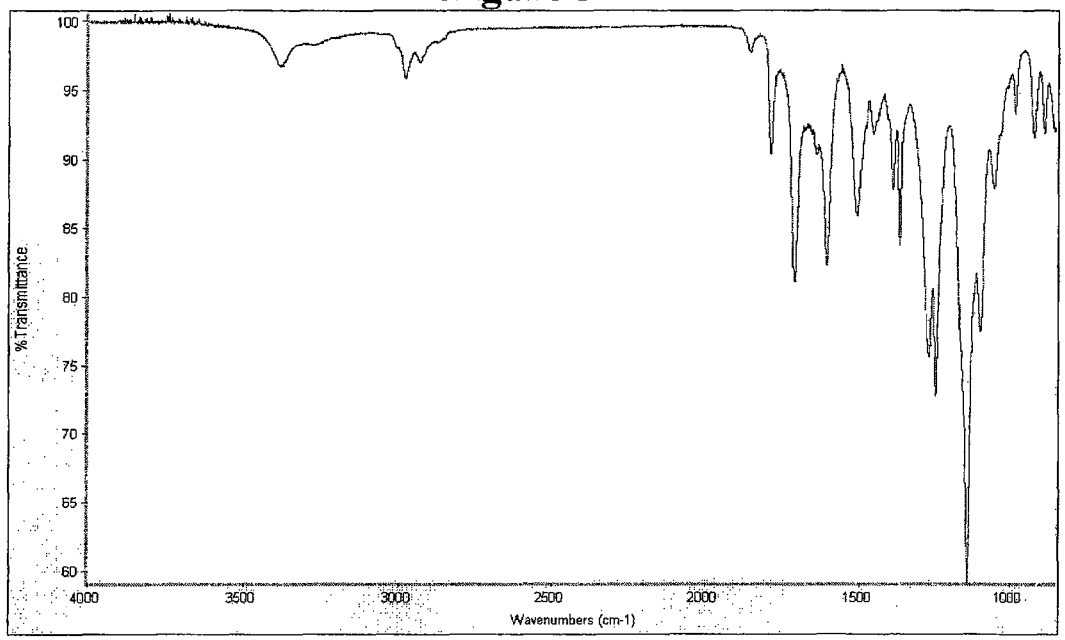
FIG. 3. An IR graph showing the Arginine-Vitamin C compound.
Figure 4:
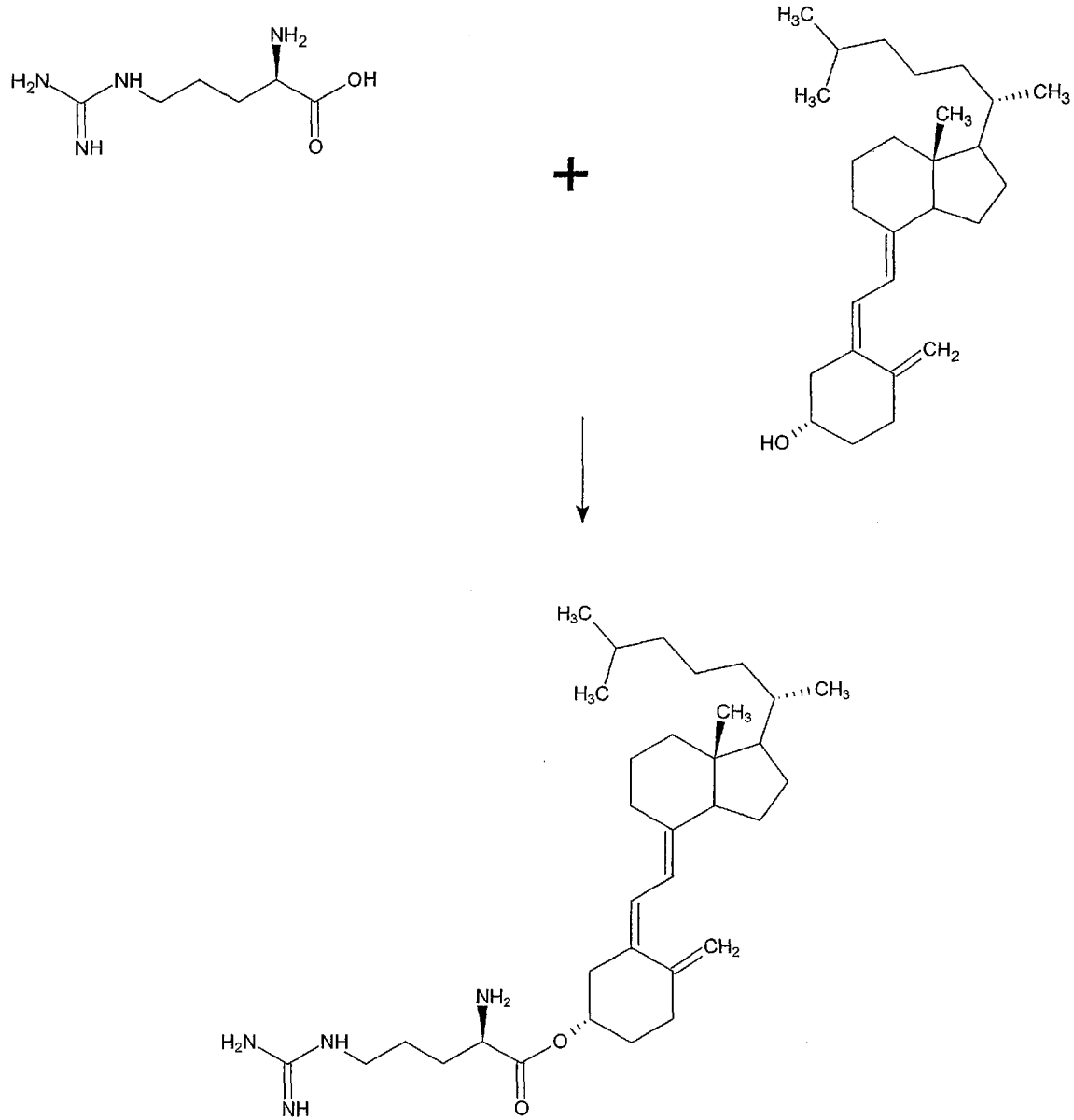
FIG. 4. Diagram showing the formation of arginine heteromer from vitamin D3.

This invention discloses a number of arginine heteromers which serve as substrates for nitric oxide synthase (with or without processing of the heteromer) and which have increased flux, with respect to native arginine, of the heteromer across skin when applied topically. In other embodiments for example, the heteromers also provide additional properties such as antioxidant activity.

The heteromers of this invention have a structure as in Formula I:

$$A\text{-}R \qquad \qquad I$$

where A is a single arginine molecule covalently bound to a second compound R. The arginine molecule may be bound through its free carboxy or amino group and the arginine guanidino group remains unreacted and free. The second compound, R, is an organic molecule that is not arginine or oligo-arginine. In an embodiment of this invention the second compound R further provides one or more of the properties selected from the group consisting of improving the solubility in oil or in water of the arginine heteromer compared to arginine alone, and improving the rate of flux of the arginine heteromer across skin compared to arginine alone. The second compound may further provide additional benefits to the skin. The second compound is compatible for contact with mammalian tissues by being non-toxic, non-allergenic and non-irritating. Examples of suitable second compounds include, but are not limited to, vitamins, retinoids and fatty acids.

Ascorbic acid (vitamin C), alpha-tocopherol (vitamin E) and retinoids (vitamin A) when used in accordance with this invention may provide beneficial properties for skin. Ascorbic acid stimulates the synthesis of connective tissue and in particular it stimulates and regulates the production of collagen. It acts to help prevent or minimize lipid oxidation and other forms of cellular damages resulting form prolonged exposure to ultraviolet rays. It is believed that ascorbic acid helps to inhibit the formation of melanin and the release of histamine from cellular membranes. Ascorbic acid compensates for vitamin E deficiency in the skin, helps prevent discoloration of the skin, and it has an anti-free radical activity. Alpha-tocopherol is an antioxidant for protecting the phospholipids of the cell membrane and harmful effects of free radicals (J. B Chazan et al. Free Radicals and Vitamin E. *Cah. Nutr. Diet.* 1987 22(1):66-76). Retinoids block mediators of inflammation in the skin and increase the production of procollagen leading to higher amounts of type I and type III collagen.

In some embodiments, the second compound is a vitamin such as vitamin A, vitamin B1, vitamin B2, vitamin B3, vitamin B5, vitamin B6, vitamin B7, vitamin B9, vitamin B12, vitamin C, vitamin D1, vitamin D2, vitamin D3, vitamin D4, vitamin D5, vitamin E, and vitamin K.

In other embodiments the second compound is a retinoid. Retinoids include retinol, natural and synthetic analogs of vitamin A (retinol), vitamin A aldehyde (retinal), vitamin A acid (retinoic acid), including all-trans, 9-cis, and 13-cis retinoic acids, etretinate, and others as described in U.S. Pat. No. 4,887,805 and U.S. Pat. No. 4,888,342 (the disclosures of which are all incorporated herein by reference). Various synthetic retinoids and compounds having retinoid activity are expected to be useful in this invention, to the extent that they exhibit retinoid activity in vivo, such as in the following U.S. Pat. Nos. 5,514,825; 5,698,700; 5,696,162; 5,688,957; 5,677,451; 5,677,323; 5,677,320; 5,675,033; 5,675,624; 5,672,710; 5,688,175; 5,663,367; 5,663,357; 5,663,347; 5,648,514; 5,648,503; 5,618,943; 5,618,931; 5,618,836; 5,605,915; 5,602,130. Still other compounds described as having retinoid activity are described in other U.S. Pat. Nos. 5,648,563; 5,648,385; 5,618,839; 5,559,248; 5,616,712; 5,616,597; 5,602,135; 5,599,819; 5,556,996; 5,534,516; 5,516,904; 5,498,755; 5,470,999; 5,468,879; 5,455,265; 5,451,605; 5,343,173; 5,426,118; 5,414,007; 5,407,937; 5,399,586; 5,399,561; 5,391,753; and the like, the disclosures of all of the foregoing and following patents and literature references hereby incorporated herein by reference.

In further embodiments of the invention, the second compound is a fatty acid. Fatty acids are monocarboxylic acids having a saturated or unsaturated aliphatic tail. As defined in the *International Cosmetic Ingredient Dictionary and Handbook,* 7th Ed. (1997) volume 2, page 1567 (the disclosure of which is incorporated herein by reference) fatty acids have about 7 or more carbon atoms. For example, palmitic acid is a saturated fatty acid found in palm oil and other fats. It is the most abundant natural fatty acid. Palmitic acid is also one of the skin's major fatty acids produced by the sebaceous glands. Palmitic acid is used in skin care and cosmetic preparations as a moisturizing agent. It normalizes skin to a normal, healthy state and stabilizes oil balance. It softens skin and acts like an antikeratinizing agent. It is also used as an emulsifier, surfactant and a formula texturizer. Esters of palmitic acid are used to impart silkiness to the skin and hair. The palmitic acid serves as a carrier to allow penetration of the pentapeptide into the skin. It is widely used as a lubricant.

In addition to palmitic acid, suitable fatty acids include, but are not limited to, undecylenic, palmitoleic, oleic, linoleic, linolenic, arachidonic and erucic acids. Additional suitable fatty acids can be found in the *International Cosmetic Ingredient Dictionary and Handbook,* 7th Ed. (1997) volume 2, page 1567.

The arginine molecule and second compound are bound by a covalent linkage. The kinds of linkages include, but are not limited to, ester, amide, ether and carbamide linkages. Embodiments of the invention include, but are not limited to, heteromers of arginine with vitamins, retinoids or fatty acids.

The arginine heteromer is delivered across the skin in an amount effective to produce a beneficial effect on the skin. As used herein, the term "beneficial effect" includes any improvement in the appearance or feel of the skin or any protective effect from damage to the skin resulting from external sources such as sunlight or from internal sources such as the effects of aging. The term "effective amount" refers to that amount of the arginine heteromer which penetrates the stratum corneum layer of the skin that is sufficient to produce the desired beneficial effect.

Once in skin, the heteromers of this invention may degrade to release arginine and the second compound. It is not necessary for the heteromer to degrade as long as the guanidino group of the arginine portion of the heteromer remains unreacted and free so that it may serve as a substrate for nitric oxide synthase. The arginine heteromers can be stabilized in formulations prior to application. Thus, higher rates of transepithelial delivery of arginine can be accomplished in a manner relevant to providing the intended beneficial effect.

The arginine heteromers of the invention may be used in a number of cosmetic or dermatological compositions intended for topical application. Because the arginine heteromers can stimulate angiogenesis in hair follicles, these compositions may be used for the prevention of hair loss or to enhance hair growth. When used to affect hair growth these compositions are applied to the scalp, eyebrows or eyelashes. The compositions may be applied to the lips to improve color and plumpness. When applied to the skin, the arginine heteromer compositions may be used to reduce the appearance of fine lines and wrinkles, improve skin elasticity, reduce puffiness, smooth skin texture, provide a silky feel to the skin, provide a moisturizing effect, provide lubrication, provide a natural blush, reduce the effects of aging or provide other cosmetic benefits.

For application to skin or lips, the arginine heteromers are included in compositions that comprise cosmetically or dermatologically acceptable carriers or vehicles that are suitable for the area of the body to which they will be applied. The term "cosmetically or dermatologically acceptable," as used herein, includes the compositions or compounds suitable for use in contact with physiologic tissues without undue toxicity, incompatibility, instability and the like.

A number of compositions and formulations typically used in products applied to the skin, lips and hair can be used with the arginine heteromers of the invention. These include but are not limited to skin-care preparations such as skin-washing and cleansing preparations, soap less detergents, body lotions, emulsions or skin oils, skin peel or scrub preparations or peeling masks; bath preparations such as liquid or solid bath preparations, bath cubes and bath salts; cosmetic personal care preparations such as facial make-up in the form of day creams or powder creams, face powder, rouge or cream make-up; eye-preparations such as eye shadow, mascara, eyeliner or eye creams; lip-care preparations such as lipsticks, lip gloss or lip contour pencils; nail-care preparations such as nail polish and nail varnish; foot-care preparations such as foot baths, foot powders, foot creams or foot balsams, special deodorants and antiperspirants or callous removing preparations; sunscreen preparations such as lotions, creams, oils, sun blocks, pre-tanning preparations, after-sun preparations, skin-tanning preparations or self-tanning creams; hair-care or hair-treatment preparations such as shampoos, conditioners, styling creams, styling gels, foams, rinses, hairsprays or hair dyes and colorants.

The compositions of the invention may be in the form of solutions, emulsions, micro emulsions, suspensions, creams lotions, gels, waxy products such as for example lipstick and powders and other solid cosmetics of various types including but not limited to antiperspirants and eyeliner.

The arginine heteromer compositions of the invention can also comprise other ingredients commonly used in skin care and hair care products such as antimicrobials, moisturizers, hydration agents, penetration agents, preservatives, emulsifiers, natural or synthetic oils, solvents, surfactants, detergents, gelling agents emollients, antioxidants, fragrances fillers thickeners waxes, odor absorbers, dyestuff, coloring agents, powders, viscosity-controlling agents, anesthetics, anti-itch agents, botanical extracts, conditioning agents, darkening or lightening agents, glitter, hair pigment additives, humectants, mica, minerals, polyphenols, silicones or silicone derivatives, sun blocks, vitamins, phytomedicinals and other compounds as listed in the *International Cosmetic Ingredient Dictionary and Handbook*, 7th Ed. (1997).

Compositions of the invention can comprise active ingredients other than the arginine heteromers. For example, anti-acne agents including but not limited to salicylic acid, benzoyl peroxide, resorcinol, and sulfur; anti-oxidants including but not limited to ascorbic acid, caffeic acid, cysteine, hydroquinone and tocopherol; compounds for the treatment of psoriasis including but not limited to salicylic acid, coal tar and retinoids; and corticosteroids including but not limited to cortisone, hydrocortisone and prednisone.

In some embodiments of the invention, the arginine heteromers are used for treating, ameliorating or preventing skin aging. Skin damage due to aging may include but is not limited to both fine and deep wrinkles, skin lines, crevices, bumps, large pores, scaliness, loss of skin elasticity, sagging, loss of skin firmness or tightness, discoloration, hyperpigmented regions such as age spots and freckles, keratosis, abnormal differentiation, hyperkeratinization, elastosis, collagen breakdown, and other histological changes in the stratum corneum, dermis, epidermis, the vascular system of the skin, and underlying tissues especially those close to the skin. The skin aging may be due to chronological aging or to extrinsic factors such as prolonged exposure to sunlight but the compositions of the invention are expected to treat, ameliorate or prevent these and other forms of skin damage regardless of the mechanism of origin.

Compositions of this invention may be in the form of products to be applied to the skin or epithelium of subjects or patients, i.e. humans or other mammals who could benefit from the treatment. The compositions and methods of this invention have pharmaceutical and/or health-related applications and may be used to provide treatment for various medical conditions to persons who might need or benefit from them. For example, inventions described herein may be used for treating hyperhidrosis, acne or other conditions involving the excess production of secretions or sweat.

In general, the compositions of this invention are prepared by mixing the arginine heteromer with a carrier, and usually with one or more additional pharmaceutically acceptable carriers or excipients. The arginine heteromer is present in the compositions at a concentration of from about 0.001% to a saturated solution, in some embodiments from about 0.01% to about 30% and in other embodiments from about 0.1% to about 20%. In their simplest form, the compositions of this invention may contain a simple aqueous pharmaceutically acceptable carrier or diluent, such as buffered saline. However, the compositions may contain other ingredients typical in topical pharmaceutical or cosmeceutical compositions, that is, a dermatologically or pharmaceutically acceptable carrier, vehicle or medium, i.e. a carrier, vehicle or medium that is compatible with the tissues to which they will be applied. The term "dermatologically or pharmaceutically acceptable," as used herein, includes compositions or components that are suitable for use in contact with specific tissues or for use in patients in general without undue toxicity, incompatibility, instability, and the like. As appropriate, compositions of the invention may comprise any ingredient conventionally used in the fields under consideration, and particularly in cosmetics and dermatology. The compositions also may include a quantity of a small anion, preferably a polyvalent anion, for example, phosphate, aspartate, or citrate.

EXAMPLES

Example 1

Purpose

To develop novel conjugations of arginine, arginine-vitamin C, for improved flux and increase therapeutic benefit.

Arg-Vitamin C Preparation:

A heteromer of vitamin C and arginine was prepared by preparing a solution of BocArg(Boc$_2$)OH (159 mg, 0.33 mmol) in dimethylformamide and adding ethylene dichloride (EDC, 70 mg., 0.36 mmol) followed by 4-dimethylaminopyridine (DMAP, 2 mg, 0.02 mmol). The reaction was stirred for 2 hours at room temperature. A TLC analysis was performed to check the progress of the reaction (vide infra). An additional 22.7 mg EDC was added and the reaction stirred for ½ hour. The reaction was observed to turn light purple. The reaction yielded 44 mg of compound 2. IR of compound was performed and is shown below. MS (ES): 1101.9, 745.6, 645.5, 630.6, 530.6, 502.4

Deprotection of C-Arg (to Remove Boc):

The Boc protective groups of compound 2 were removed by preparing a solution of 25 mg compound 2 in dichloromethane (~10 ml) and adding 2 ml trifluoroacetic acid while stirring in an ice bath. The mixture was stirred for ~1 hour then allowed to warm to room temperature. TLC (10% MeOH/dichloromethane) after 2 hours at room temperature showed loss of starting material and strengthening of the origin (product) spot. Compound 4 afforded a UV active spot of modest Rf in that solvent system. Solvent was removed under reduced pressure and the residue was azeotroped with twice with toluene to give 25 mg of compound 4.

Results:

This experiment demonstrates the synthesis of Arginine-Vitamin C compound.

Example 2

Procedure

Figure 5:
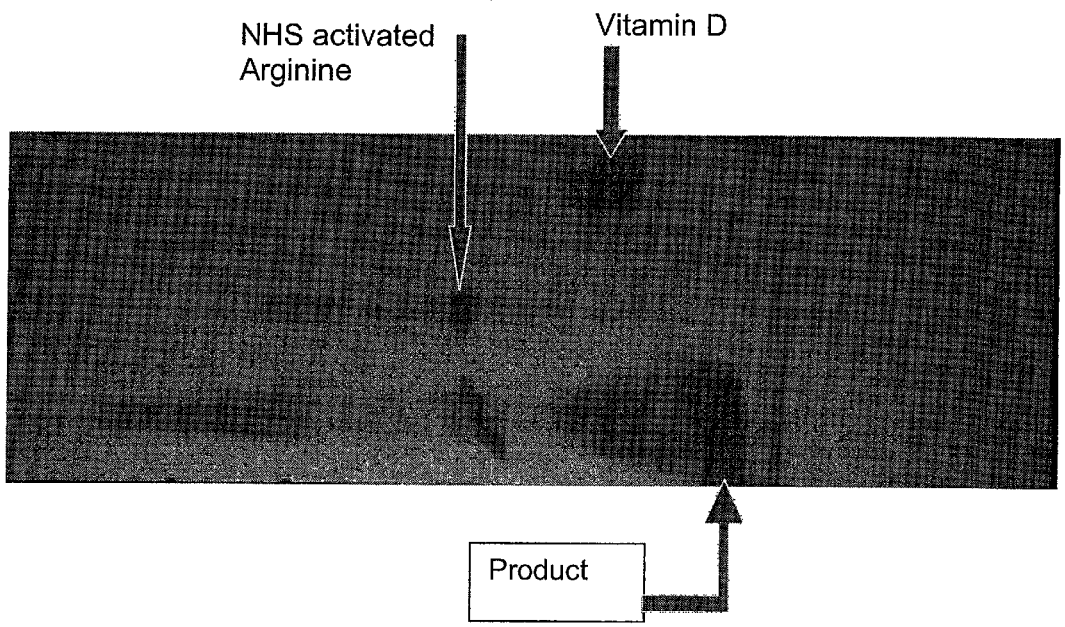
FIG. 5. A TLC showing the Arg-Vit D3 product.

A heteromer of arginine and vitamin D3 was prepared by dissolving triphosgene (0.1 g, 0.33 mmole) in 1 ml anhydrous methylene chloride. The triphosgene solution was added dropwise to a cooled solution (0 degrees) of vitamin D3 (0.385 g, 1 mmole) and DMAP (0.61 g, 5 mmole) in 2 ml methylene chloride. The reaction mixture was allowed to stir at zero degrees for 1.5 hours. A mixture of L-Arginine (0.261 g, 1.5 mmole) and N,N-Diisopropylethylamine (523 ul, 3 mmole) was added dropwise to the triphosgene mixture. The reaction was allowed to warm to room temperature overnight and yielded 205 mg white solid (35% yield). This experiment demonstrates the synthesis of Arginine-Vitamin D3 heteromer and the TLC is shown in FIG. 5.

Example 3

In vivo cumulative efficacy for topical delivery of arginine across murine skin.

Purpose:

The potential for a heteromer of arginine to cross the skin and exert previously characterized benefits related to arginine/NOS activity was evaluated by examining arginine-vitamin E and arginine-palmitate heteromers in an animal model system. While both heteromers improve the lipid solubility relative to arginine alone and should increase transdermal flux, the vitamin E heteromer is also expected to afford additional functional benefits due to its anti-oxidant properties.

Preparation:

Arginine-palmitate and arginine-vitamin E heteromers were synthesized from L-arginine (Batch #02202JA, A92406-25G, Sigma Aldrich). The stock solutions were prepared by adding the following:

1. Arg-palmitate: 0.9996 g of arginine+palmitate were dissolved in 6 ml of jojoba oil (Essential Wholesale, Portland, Oreg.), then diluted with 6 ml (1:1 dilution) of Cetaphil cream.

2. Arg-vitamin E: 0.419 g of arginine+vitamin E were dissolved in 6 ml of deionized $H_2O$ then diluted with 6 ml (1:1 dilution) of Cetaphil cream.

3. Cetaphil: prepared with 6 ml of cetaphil only.

Daily-dose topical treatments of metered 200 µl aliquots were prepared for treatments of Arg-palmitate, Arg-vitamin E, or Cetaphil control in 650 µl microcentrifuge tubes.

Topical Application of Arginine Compounds

Study Procedures:

Animals (C57 black 6 female mice, Charles River Laboratories, Wilmington, Mass.) were anesthetized via inhalation of isoflurane mixed with oxygen and then injected with 0.5 ml rodent anesthetic cocktail (3.75 ml of 100 mg/ml Ketamine, 3.00 ml of 20 mg/ml Xylazine, and 23.25 ml of saline) intraperitoneally. The animals were supplemented with isoflurane as necessary. Treatment groups contained 4 mice each and the control group 3 mice. After being anesthetized, a 2.0 cm×2.0 cm dose site on the dorsum of each mouse was carefully shaved with a hair clipper on the first day of treatment application and animals underwent depilatory treatment in the same dorsal region using a rosin mixture (Surgiwax, Ardell International, Los Angeles, Calif.). Animals were anesthetized via inhalation of isoflurane only during the application of treatments in Cetaphil moisturizing cream (Galderma, Fort Worth, Tex.) and had metered 200 µl doses of the appropriate treatment applied to the cranial portion of dorsal back skin (selected because the mouse cannot reach this region with mouth or limbs). Animals remained under anesthesia for 1-2 minutes while the appropriate treatment was applied into the skin with small metal spatula. Animals recovered in a controlled heat environment to prevent hypothermia and once responsive were provided food and water ad libitum overnight. This procedure was repeated once daily at the same approximate time of day for 7 days. After the day 7 treatment, mice were euthanized via inhalation of $CO_2$, and treated skin segments were harvested at full thickness by a blinded observer at 24 hours post application of the last treatment. Treated segments were divided into three equal portions and the cranial portion was fixed in 10% neutral buffered formalin for 12-16 hours then stored in 70% ethanol until paraffin embedding. The central portion was employed for Hematoxylin & Eosin for morphological assessment and Chloroacetate esterase staining to evaluate neutrophil infiltration as an indicator of inflammation. The treated caudal segment was snap frozen for solubilization studies.

Image and Statistical Analysis:

High resolution digital images of each section were obtained using a Retiga 1300B camera (QImaging, Burnaby, BC, Canada). Images were analyzed using Image-Pro Plus analysis software (Media Cybernetics, Silver Springs, Md.) to determine morphological assessment and expressed as positive pixels. Mean and standard error were subsequently determined for each group using Statview software (Abacus, Berkeley, Calif.), with analysis of significance at 95% confidence in Wilcoxon signed ranks.

Results for Arg-Palmitate and Arg-Vitamin E:

Mean, standard error, and p-values are shown in Table 1 for groups Arg-palmitate, Arg-vitamin E and control.

Table 1. The morphological assessment of dermal thickness, hair length, epidermal thickness, fat thickness/density.

TABLE 1

|  | Mean | Std. Error | P value |
|---|---|---|---|
| Dermis: | | | |
| Arg-palmitate | 32596 | 1398 | 0.596 |
| Arg-Vitamin E | 35779 | 1425 | 0.038 |
| Control | 31405 | 1959 | |
| Hair: | | | |
| Arg-palmitate | 17149 | 1908 | 0.668 |
| Arg-Vitamin E | 18316 | 1502 | 0.044 |
| Control | 15613 | 1186 | |

TABLE 1-continued

|  | Mean | Std. Error | P value |
|---|---|---|---|
| Epidermis: | | | |
| Arg-palmitate | 11086 | 749 | 0.939 |
| Arg-Vitamin E | 16475 | 1513 | 0.0004 |
| Control | 11082 | 890 | |
| Fat: | | | |
| Arg-palmitate | 27918 | 2662 | 0.820 |
| Arg-Vitamin E | 21386 | 1092 | 0.007 |
| Control | 27419 | 1849 | |

Conclusions:

Arginine heteromers have sufficient flux across skin when applied topically to afford several therapeutic benefits related to arginine and/or the additional functionality of the heteromer.

Example 4

Purpose

The potential for a heteromer of arginine to cross the skin and exert previously characterized benefits related to arginine/NOS activity was evaluated by examining several arginine heteromers in a human model system. All heteromers improve the lipid solubility relative to arginine alone and should increase transdermal flux and perfusion.

Procedure:

Flowmeter Probe Modification and Arginine Heteromer Formulations

Lip balm formulations were obtained consisting of Anhydrous Lanolin USP, Ethyl Methylphenylglycidate, Cetyl Esters, D-Alpha Tocopheryl Acetate USP, Petrolatum USP, Salicylic Acid USP, Benzyl Cinnamate and 4.0 mg/ml of either L-Arg(9) (an oligomer consisting of nine arginines), L-Arg-E, L-Arg-$D_3$ or L-Arg-Palm (ABBE Labs, Farmingdale, N.Y.). In addition, a control treatment was obtained comprised of 100% white Petrolatum jelly (Unilever, Greenwich, Conn.). Aqueous solution of L-Arg at 50 mg/ml (Sigma-Aldrich, St. Louis, Mo.) concentration was used. The probe tip of a Transonic Laser Doppler Flowmeter BLF 21 Series (Transonic Systems, Ithaca, N.Y.) was implanted in an elastic headband such that the probe was lightly held on a section of skin in the middle of the subject's forehead.

Forehead Treatment

Forehead temperature was normalized prior to treatment by wearing the modified headband for five minutes. A lip balm formulation or control was then applied with cotton tipped applicator to the area of skin in contact with probe. Tissue perfusion readings were recorded every 30 seconds for 5 minutes (n=55 per treatment) beginning one minute after application.

Statistical Analysis

Mean and standard error were assessed using Statview (Abacus Concepts, Berkeley, Calif.), with comparisons made using ANOVA repeated measures and significance determined at 95% with post-hoc testing using Fisher PLSD or Scheffe F-test. All procedures and analyses were performed by blinded observers.

Figure 6:
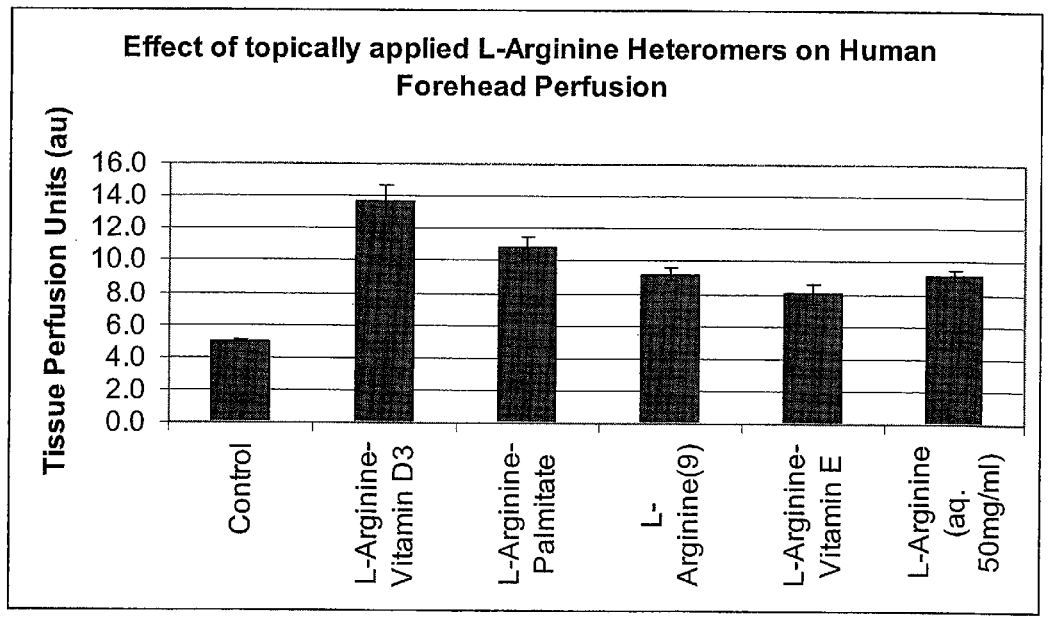
FIG. 6. Effect of topically applied L-Arginine heteromers on human forehead perfusion.

Results of Forehead Perfusion:

Mean, standard error, and p-values are shown in Table 2 for arginine heteromer groups and control. FIG. 6 shows effects of topically applied arginine heteromers on human forehead perfusion for arginine heteromer groups and control.

TABLE 2

Forehead perfusion assessment in tissue perfusion units following topical arginine heteromer treatment.

|  | Mean | Std. Error | P value |
|---|---|---|---|
| L-Arg-$D_3$ | 13.727 | 0.9956 | $p < 0.05$ |
| L-Arg-Palm | 10.800 | 0.7188 | $p < 0.05$ |
| L-Arg(9) | 9.198 | 0.4003 | $p < 0.05$ |
| L-Arg-E | 8.016 | 0.5719 | $p < 0.05$ |
| aqueous L-Arg (50 mg/ml) | 9.184 | 0.3009 | $p < 0.05$ |
| Control | 4.987 | 0.0621 | |

Conclusion:

All heteromers caused statistically significant increases in perfusion with respect to the base control. L-Arg-$D_3$ and L-Arg-Palm, which exhibited 175% and 117% increases respectively in tissue perfusion over the base control. Encouragingly, we find that all of the heteromers have greater solubility and flux across skin, while all but L-Arg-E exhibit increased perfusion after topical application. Arginine heteromers have sufficient flux across skin when applied topically to afford several therapeutic benefits related to arginine and/or the additional functionality of the heteromer.

What is claimed is:

1. A topical composition comprising a heteromer of formula I:

$$A\text{-}R \qquad \text{I}$$

wherein A is arginine and R is retinoic acid, and A and R are covalently bound by an amide linkage via an amino group of the arginine, such that the guanadino group of the arginine remains unreacted, wherein the heteromer has greater flux across the skin than arginine alone; and wherein the topical composition further comprises a dermatologically acceptable carrier or vehicle for topical application.

2. The composition of claim 1 further comprising skin-care preparations.

3. The composition of claim 1 further comprising bath-preparations.

4. The composition of claim 1 further comprising cosmetic preparations.

5. The composition of claim 1 further comprising eye-care preparations.

6. The composition of claim 1 further comprising lip-care preparations.

7. The composition of claim 1 further comprising sunscreen preparations.

8. The composition of claim 1 further comprising hair care preparations.

9. The composition of claim 1 further comprising an anti-acne preparation.

10. The composition of claim 1 further comprising antioxidant preparations.

11. The composition of claim 1 further comprising antipsoriasis preparations.

12. The composition of claim 1 further comprising corticosteroid preparations.

* * * * *

UNITED STATES PATENT AND TRADEMARK OFFICE
CERTIFICATE OF CORRECTION

| | | |
|---|---|---|
| PATENT NO. | : 8,815,954 B2 | Page 1 of 1 |
| APPLICATION NO. | : 11/617551 | |
| DATED | : August 26, 2014 | |
| INVENTOR(S) | : Waugh | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 134 days.

Signed and Sealed this
Twenty-ninth Day of September, 2015

Michelle K. Lee
*Director of the United States Patent and Trademark Office*